United States Patent [19]
Asai et al.

[11] Patent Number: 5,454,882
[45] Date of Patent: Oct. 3, 1995

[54] PROCESS FOR CONTROLLING A FLUORIDE CONTAINING CONVERSION COATING FORMING COMPOSITION DURING ITS USE FOR CONVERSION COATING ALUMINUM CONTAINING METAL

[75] Inventors: Yasuo Asai, Chiba; Yuzuru Matsubara, Tokyo; Hitoshi Ishi, Kanagawa, all of Japan

[73] Assignee: Henkel Corporation, Plymouth Meeting, Pa.

[21] Appl. No.: 256,498

[22] PCT Filed: Dec. 31, 1992

[86] PCT No.: PCT/US92/11099

§ 371 Date: Jul. 13, 1994

§ 102(e) Date: Jul. 13, 1994

[30] Foreign Application Priority Data

Jan. 13, 1992 [JP] Japan .................................. 4-024429

[51] Int. Cl.⁶ .................................................. C23C 22/06
[52] U.S. Cl. ........................................ 148/241; 148/262
[58] Field of Search .............................................. 148/241

[56] References Cited

FOREIGN PATENT DOCUMENTS

| | | |
|---|---|---|
| 0162489 | 11/1985 | European Pat. Off. . |
| 0304108 | 2/1989 | European Pat. Off. . |
| 0434358 | 6/1991 | European Pat. Off. . |
| 1341220 | 12/1973 | United Kingdom . |
| 9113186 | 9/1991 | WIPO . |

*Primary Examiner*—Sam Silverberg
*Attorney, Agent, or Firm*—Ernest G. Szoke; Wayne C. Jaeschke; Norvell E. Wisdom, Jr.

[57] ABSTRACT

The invention is a method for the accurate control of the conversion film thickness produced on aluminiferous metal materials by fluorine-containing acidic conversion treatment baths; and a simple method for determining the EFC value (Effective Fluorine Concentration). The EFC value is determined by potentiometric titration of a fluorine-containing acidic conversion treatment bath having pH<4 without prior pH adjustment using a fluorine ion electrode as indicator electrode. The titrant is an aqueous solution containing the Al ion, La ion, Y ion, Zr ion, Ga ion, Ce ion, or Be ion, an inflection point in the potential curve is used as an indication of the activity of the conversion treatment bath.

9 Claims, 2 Drawing Sheets

PROCESS FOR CONTROLLING A FLUORIDE CONTAINING CONVERSION COATING FORMING COMPOSITION DURING ITS USE FOR CONVERSION COATING ALUMINUM CONTAINING METAL

FIELD OF THE INVENTION

The invention relates to a method for surface treatment of aluminiferous metal-containing structures with acidic conversion treatment baths. The method is particularly useful for treating the surfaces of car bodies, household electrical appliances, and the like, with phosphate conversion coating baths, chromate treatment baths, and they like. Particularly, the present invention relates to a method for reproducibly controlling the chemical activity of fluorine in conversion treatment baths.

BACKGROUND OF THE INVENTION

The addition of fluorine to acidic conversion treatment baths for treating aluminiferous metal-containing structures is well known. One example of this methodology is taught in Japanese Patent Application Sho 63-157879 (157,879/1988).

RELATED ART

The fluoride ion concentration in an aqueous solution is generally measured directly using a fluorine ion meter. Japanese Patent Application Sho 63-17879 discloses a measurement method that relates to phosphate conversion treatment solutions. In the disclosed method, the fluoride ion concentration in a sample is measured after calibration of the fluorine ion electrode with fluorine reference solutions of known fluorine ion concentration. Using the fluoride ion concentration calculated based on the results of this measurement the phosphate conversion treatment is operated by adjusting the bath components to maintain the fluoride ion concentration within a specified range.

A chromate conversion treatment wherein the fluoride ion concentration is maintained within a prescribed range is disclosed in Japanese Patent Application Hei 3-48271 (48, 271/1991).

Although not intended for controlling the activity of conversion treatment baths, a method is disclosed in Z. Anal. Chem. 245 67 (1969) for the measurement of fluorine concentration through a potentiometric titration which uses a fluorine ion electrode as indicator electrode, and an aluminum nitrate solution, lanthanum nitrate solution, or the like as titrant. The method measures the total fluorine content in aqueous solutions, and requires that the sample be pre-treated by adjustment of the pH to a range of 4 to 7.

Several problems are associated with direct concentration measurement of the fluoride ion concentration in acidic conversion treatment baths using a fluorine ion meter. The fluorine ion electrode ultimately degrades with time during the measurement process, which necessitates frequent calibration with, reference solutions. Moreover, due to a progressive deterioration of the fluorine ion electrode, the current state of the art of measurement of fluoride ion concentration in acidic aqueous solutions requires frequent performance of complex operations such as washing the electrode, electrode calibration and the like.

However, even when the fluoride ion concentration is accurately measured and maintained the conversion film thickness and the coating add-on per unit area is subject to substantial variations when conversion treatment is operated continuously while holding the fluoride ion concentration as well as other managed parameters (e.g., pH, total acidity) at their respectively prescribed values. Since the film weight is an indication of the conversion treatment performance, in conversion treatments such as zinc phosphate conversion treatment, the film weight value can be taken as an index of the conversion treatment performance. When conversion treatment is implemented based on the fluoride ion measurement instability is observed not only in the corrosion resistance and paint adherence of the treated substrate, but also in the corrosion resistance and adherence of the paint film.

Methods based on potentiometric titration as disclosed in Z Anal. Chem. 245 67 (1969), offer the advantages of no troublesome fluorine ion electrode calibration and low measurement error due to electrode deterioration. However, due to the preliminary adjustment of the sample pH to the range of 4 to 7, the fluoride ion concentration measured by this method is the total fluorine concentration, and the concentration of fluorine effectively available for participation in conversion treatment cannot be measured. Since the total fluorine concentration is not necessarily a parameter that controls the conversion characteristics of acidic conversion treatment processes, the method is unsuitable as a means for controlling acidic conversion treatment processes and therefore suffers from the same problems the method of Japanese Applicant Sho 63-157,879.

BRIEF DESCRIPTION OF THE INVENTION

Extensive research was conducted in order to solve the problems in the prior art method. Methods were examined for measuring the concentration of fluorine effectively available for participation in the conversion process (component in acidic conversion treatment baths that contributes to the conversion process). It was confirmed that the fluorine concentration that effectively contributes to the conversion reactions can be rapidly and reproducibly measured while at the same time countering deterioration of the fluorine ion electrode. According to the invention, the fluorine concentration which contributes to the activity of an acidic conversion treatment bath having a pH below about 4 is directly potentiometrically titrated, without pH adjustment, using a fluorine ion electrode as indicator electrode and using as titrant an aqueous solution containing aluminum ion, lanthanum ion, yttrium ion, zirconium ion, gallium ion, cerium ion, or beryllium ion. The effective fluorine concentration (EFC) is determined from the quantity of titrant addition up to the inflection point on the potential curve of the fluorine ion electrode. The problems associated with the prior art are solved by operating conversion treatment processes based on this measurement method.

The EFC value afforded by the measurement method of the present invention has a better correlation with the conversion process in acidic conversion treatment baths than the fluoride ion concentration values measured heretofore (detection of the total fluorine concentration or free fluoride ion concentration).

DETAILED DESCRIPTION OF THE INVENTION

Figure 1:
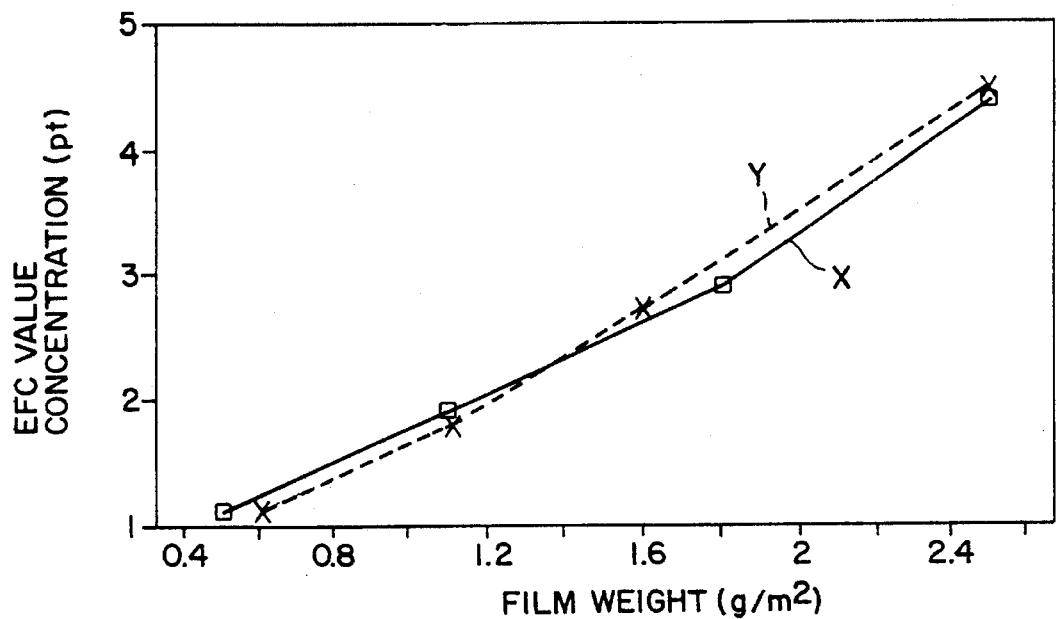
FIG. 1 is a graph of the relationship between the EFC (points) and the Film Weight.

The present invention was developed based in the discovery that with respect to a process for acidic conversion treatment of alumininferous metal, the process can be improved by monitoring the EFC in a fluorine-containing, acidic conversion treatment bath having pH <4 by potentiometrically titrating samples of the bath, without prior pH adjustment, using a fluorine ion electrode as indicator electrode and using as titrant an aqueous solution containing at least one of aluminum ion, lanthanum ion, yttrium ion, zirconium ion, gallium ion, cerium ion, or beryllium ion and measuring the quantity of titrant addition up to the inflection point on the potential curve for the fluorine ion electrode and adding a fluorine-containing chemical to the bath when the EFC falls below a specified range.

The conversion treatment bath used in the practice of the invention can be a phosphate conversion treatment bath or chromate treatment bath. The method is effective for all bath compositions which contain fluoride known to be useful for conversion treatment of aluminum and aluminum alloys. The bath compositions are not particularly restricted. Operative conversion treatment baths are, for example, the phosphate conversion treatment bath disclosed in Japanese Patent Publication Hei 3-38343 (38,343/1991) by the present applicant and the chromate treatment bath disclosed in Japanese Patent Publication Sho 63-66906 (66,906/1988) by the present applicant.

According to the present invention, the particular conversion treatment is operated while maintaining the EFC value determined by the measurement method described hereinafter (points of effective fluorine concentration EFC value) within a predetermined range. The EFC value is preliminarily determined as a function of the type of conversion treatment, bath composition, metal being treated, temperature and .other parameters known to those skilled in the art. When the EFC value (points) exceeds the upper limit of the predetermined range, metal etching by fluoride becomes excessive and the resulting conversion film is heavier than required. When the EFC value (points) falls below the lower limit of the predetermined range, etching of the metal by the fluoride is inadequate and an adequate conversion coating is not formed. A characteristic feature of the present invention is the maintenance of the EFC value in a desired range in the conversion treatment bath, by the addition of a fluorine-containing composition such as, for example, fluoroboric acid, fluoroborate, hydrofluoric acid, sodium fluoride, sodium fluorosilicate and fluorosilicic acid.

In addition, the parameters ordinarily measured and controlled during conversion treatment processes such as the pH, total acidity, redox potential, and the like, must still be measured, and controlled at the same time as the EFC value is measured and controlled. Methods for measuring the parameters of a conversion treatment bath are known, and, for example, are described in Japanese Patent Publication Number Hei 3-59989 (59,989/1991).

The method for measuring the EFC value (points of effective fluorine concentration) is as follows:

1. A known quantity (A, mL) of the acidic conversion treatment bath is taken as the sample.
2. Optionally, the sample can be diluted.

The sample (a known quantity of acidic conversion treatment bath) may be optionally diluted with a liquid that does not form compounds with fluorine, such as pure water, ethanol and the like.

3. A fluoride ion electrode is brought into contact with the sample of the treatment bath. The fluoride ion electrode useful in the practice of the invention must show a variation in emf as a function of the fluoride ion concentration in the treatment bath. (Since the method of the invention does not require measurement of the total fluoride ion concentration, calibration of the fluorine ion electrode with a fluoride ion reference solution is not required.)
4. The sample of the acidic conversion treatment bath is then titrated using as titrant an aqueous solution that contains aluminum ion, lanthanum ion, yttrium ion, zirconium ion, gallium ion, cerium ion, or beryllium ion (B, mol/L).
5. The relationship between the quantity of titrant and the electromotive force (emf) of the fluoride ion electrode is plotted as a titration curve, and the quantity of titrant up to the inflection point on the titration curve is determined (C, mL). The titration curve denotes a graphical plot on the two coordinate axes of the electromotive force (E,mV) of the fluoride ion electrode and the quantity of titrant addition (V,mL). The inflection point on the titration curve is the point at which the value of dE/dV (differential value for the electromotive force) determined from the graph passes through a relative maximum. The values of A and B in this measurement procedure are not specifically restricted, although of course they will have optimal ranges.
6. Using the values of A, B, and C, the EFC value (points) is calculated using Equation 1.

Equation 1

Points of Effective

Fluorine Concentration (EFC) $= 400 \times B \times C / A$

As an example, when 20 mL is used for A (sample size) and 0.05 mol/L is used for B, the value of C (mL) is then equivalent to the EFC value (points of effective fluorine concentration).

The water-soluble metal salts used as the titrant comprise, for example, the nitrates, sulfates, chlorides, or other water soluble salts of the specified metals. The concentration of the water-soluble salt may be adjusted as necessary as a function of the sample size and fluorine concentration in the sample, but is preferably approximately 0.01 to 0.1 mol/L in the case of acidic conversion treatment baths such as zinc phosphate conversion treatment baths, chromate treatment baths, and the like. At below 0.01 mol/L, the potential of the fluoride ion electrode undergoes only a slow variation with respect to the amount of titrant added. Conversely, at values above 0.1 mol/L, the electrode potential varies so sharply that it becomes difficult to determine the inflection point in the titration curve. The treatment bath sample is optimally approximately 10 to 100 mL in order to be convenient for automatic titration.

The fluorine component in acidic conversion treatment baths makes a major contribution to the etching of the metal workpiece being treated. In the particular case of aluminum and aluminum-containing metal workpieces, the fluorine component has a substantial effect on the conversion treatment process. However, the conversion activity is not determined simply by the total fluorine concentration in the treatment bath, but depends on the bath's EFC value, i.e., on the concentration of fluorine that is active with respect to the metal workpiece being treated. In addition, measurement must be carried out without altering the pH of the treatment bath because the EFC value changes with pH.

Although it is a general practice to directly measure the fluoride ion concentration in aqueous solutions using a fluoride ion electrode, fluoride ion meter, and calibration with fluoride reference solutions, in this particular procedure the electromotive force of the fluoride ion electrode declines over the course of long-term application. The electrode cannot tolerate long-term service and a deteriorated electrode does not yield accurate measurement values.

The present invention measures the EFC value at the treatment bath pH by using a sample of the treatment bath itself as the sample solution. Moreover, the present invention employs measurement by a titration technique in order to counter electrode deterioration.

In the measurement method according to the present invention, a fluoride ion electrode is first brought into contact with a sample of the treatment bath. An aqueous solution that contains a known concentration of aluminum ion, lanthanum ion, yttrium ion, zirconium ion, gallium ion, cerium ion, or beryllium ion is then dripped into the sample of treatment bath. Each of these metal salts forms a complex with the fluoride ion in the treatment bath, and the fluoride ion concentration in the treatment bath therefore declines in proportion to the amount of metal ion in the titrant.

Accordingly, in the case of the fluoride ion electrode used as indicator electrode in the present invention, the fluoride ion concentration is not directly calculated from the electrode's electromotive force; rather, the fluoride ion concentration in the sample being titrated, which declines during the course of titration, is measured by examining only the change in electrode emf and determining therefrom an inflection point, which is used to determine the end point of a titration as described above. This serves to avoid the problems associated with the decline in electrode emf that is caused by electrode deterioration, during long-term service.

The use of the inflection point in the titration curve, as the titration end point, makes it possible to determine the titration end point by a simple procedure and to determine the EFC value (points) which closely correlates with the conversion performance of an acidic conversion treatment bath.

Stable conversion treatment performance can be provided by managing the bath components so as to maintain the EFC value (points) by the aforementioned method within a prescribed range. Generally the EFC is maintained in the range from about 0.70 to about 7.5 (pt.), preferably in the range of about 0.9 to about 6.5, and most preferably in the range from about 1.1 to about 4.4.

Several specific examples of embodiments of the method of the invention are provided to further illustrate the method of the invention.

First, the EFC value (Points of Effective Fluorine Concentration), the fluoride ion concentration, and the total fluorine concentration were determined by the measurement methods described below, on 4 zinc phosphate conversion treatment baths (PB-L3020 from Nihon Parkerizing Company, Limited) that were differentiated by their different fluorine containing component.

Table 1 reports the fluorine component systems in the zinc phosphate conversion treatment baths. Table 2 reports the measurement results for the fluorine concentrations of the treatment baths (immediately after the beginning of measurement and at 100 measurements at the rate of one measurement a day) and the measurement results for the film weight on an aluminum alloy plate (JIS-5052) treated at the time the EFC value measurement was made.

TABLE 1

| | Treatment Bath | | | |
|---|---|---|---|---|
| | A | B | C | D |
| Total Fluorine Concentration (ppm) | 1000 | 250 | 2000 | 600 |
| Additive System For The Fluorine Component | Fluorosilicic Acid | Hydrofluoric Acid | Fluorosilicic Acid | Hydrofluoric Acid |

Method For Measuring The EFC value (points)
1) 20 mL of acidic conversion treatment bath was taken as sample.
2) The sample was diluted with deionized water to 50 mL.
3) A fluoride ion electrode (model 7200–0.65W from DKK) was inserted in the sample.
4) Titration was carried out using 0.05 mol/L aqueous aluminum nitrate.
5) The relationship between the quantity of titrant and fluoride ion electrode emf was plotted as a titration curve, and the quantity of titrant (mL) up to the inflection point on the titration curve was taken as the EFC value (points of effective fluorine concentration).

Method for measuring the fluoride ion concentration
1) 100 ppm and 1,000 ppm fluoride ion reference solutions were prepared by the addition of sodium fluoride to 1.0 mol/L aqueous sodium nitrate, and the pH of the solution was adjusted to 5 using nitric acid or sodium hydroxide.
2) A fluoride ion electrode (model 7200–0.65W from DKK) was calibrated with the fluoride ion reference solutions.
3) The calibrated fluoride ion electrode was inserted directly into the acidic conversion treatment bath and the fluoride ion concentration was measured from the electrode emf.

Only step 3) was executed for the second and subsequent measurements

Method For Measuring The Total Fluorine Concentration
1) 20 mL of acidic conversion treatment bath was taken as a sample.
2) The sample was adjusted to pH 5 with aqueous sodium hydroxide and brought to 50 mL with deionized water.
3) A fluoride ion electrode (model 7200–0.65W from DKK) was inserted in the sample.
4) Titration was carried out using 0.05 mol/L aqueous aluminum nitrate.
5) The quantity of titrant for complete consumption of the fluorine component was determined from the potentiometric titration curve for the fluoride ion electrode. The total fluorine concentration was calculated using a consumption of 3 mol fluorine per 1 mol aluminum.

The data from the determinations are shown in Table 2.

TABLE 2

| | Treatment Bath | | | |
|---|---|---|---|---|
| | A | B | C | D |
| First Day | | | | |
| EFC value (pt) | 1.1 | 1.9 | 2.9 | 4.4 |
| Fluoride Ion Concentration (ppm) | 72 | 111 | 154 | 273 |
| Total Fluorine Concentration (ppm) | 788 | 196 | 1876 | 491 |
| Film Weight (g/m$^2$) | 0.5 | 1.1 | 1.8 | 2.5 |
| 100th Day | | | | |
| EFC value (pt) | 1.1 | 1.8 | 2.7 | 4.5 |

TABLE 2-continued

|  | Treatment Bath | | | |
| --- | --- | --- | --- | --- |
|  | A | B | C | D |
| Fluoride Ion Concentration (ppm) | 115 | 174 | 246 | 406 |
| Total Fluorine Concentration (ppm) | 790 | 199 | 1885 | 494 |
| Film Weight (g/m²) | 0.6 | 1.1 | 1.6 | 2.5 |

The data in Table 2 illustrates that the film weight provided on the aluminum alloy plate, varied as a function of the fluorine component in the zinc phosphate conversion treatment bath (acidic conversion treatment bath).

Although the film weight varied little between the 1st and 100th day, the Fluoride Ion Concentration underwent large increases. The Total Fluorine Concentration remained steady over the period for a particular bath composition. However, the Total Fluorine Concentration relationship to the coating weight is dependent on the source of fluorine. The Total Fluorine Concentration cannot be used to predict the activity of a conversion treating bath unless the source of fluorine remains constant during the life of the bath. As can be seen from a comparison of Treatment Baths A and C where the initial fluorine source was fluorosilcic acid, with Treatment Bath B and D where the initial fluorine source was hydrofluoric acid, the Total Fluorine Concentration bears no relation to the activity of the Conversion Treatment baths over the various initial sources of fluorine.

In contrast to the Fluoride Ion Concentration and total Fluorine Concentration, the EFC value measured according to the present invention, provides a measurement which closely correlates with the conversion activity of the treatment bath independently of the source of fluorine. The method of the invention is a general method and is useful for monitoring the conversion treating activity of any of the conversion treating baths, the activity of which relies on the presence of an active form of fluorine. The method of the invention measures the effective fluorine species in the bath and therefore closely correlates with the conversion activity of the bath. The close correlation can be readily seen from the graph of FIG. 1.

The data confirms that conversion treatment processes based on Fluoride Ion Concentration or Total Fluorine Concentration cannot provide a stable conversion treatment performance. In contrast, the film weight and the EFC value measurement underwent very similar variations.

Figure 2:
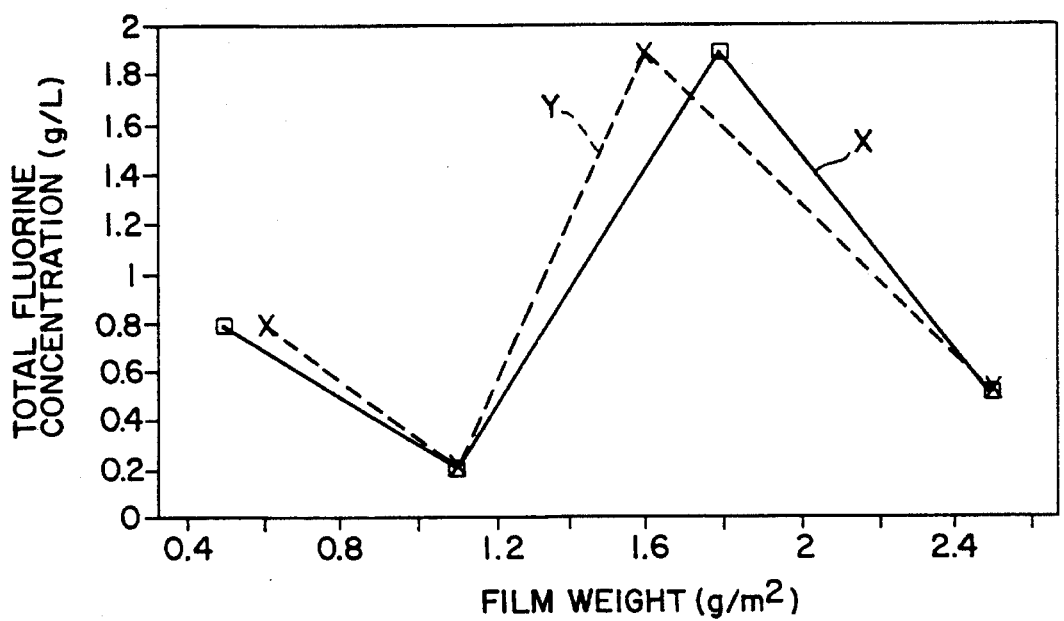
FIG. 2 is a graph of the relationship between the Total Fluorine concentration and the Film Weight.
Figure 3:
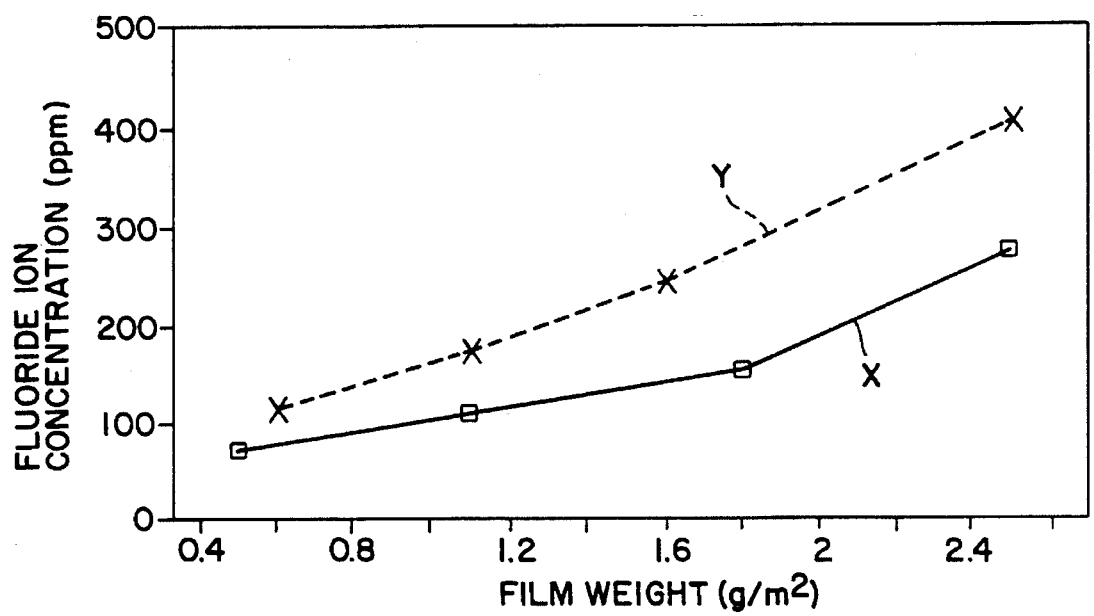
FIG. 3 is a graph of the relationship between the Fluoride Ion concentration and the Film Weight.

In order to clarify these trends, the relationships between the film weights and values measured by the methods of Example 1 are plotted in FIGS. 1, 2, and 3, respectively. In the graphs in FIGS. 1, 2 and 3, X designates the measurement values immediately after the start of measurement and Y designates the measurement values at the 100th day.

Based on these plots, the EFC value (points) exhibits a correlation coefficient with the film weight of >0.99 for both X and Y. Not only does this parameter exhibit a good correlation, but it also exhibits good reproducitility since the X and Y plots are very similar. In contrast, measurement of the, Total Fluorine Concentration, while exhibiting reproducibility, has a correlation coefficient <0.20 for both X and Y, which indicates a poor correlation with film weight. Finally, measurement of the Fluoride Ion concentration has a correlation coefficient of ≧0.95 for both X and Y; however, this method suffers from problems with measurement reproductibility since the Fluoride Ion Concentration values of the X and Y plots are widely separated.

Example 2

Based on the results from the preliminary tests, a zinc phosphate conversion treatment, as outlined below, was run on aluminum sheet (70×150×6 −8 mm). The bath was managed so as to yield film weights of 0.5 to 1.5 g/m² by using a range of 1.9 to 2.5 for the EFC valued (points). The conversion treatment was carried out as follows:

(1) Degreasing of aluminum sheet
  Fine Cleaner L4460 (strong alkaline degreaser from Nihon Parkerizing Company, Limited) 43° C., 120 seconds, spray
(2) Water Rinse (tapwater)
  room temperature, 30 seconds, spray
(3) Surface Conditioning
  Prepalene-ZN (titanium colloid surface conditioner from Nihon Parkerizing Company, Limited) room temperature, 20 seconds, spray
(4) Zinc phosphate conversion treatment
  43° C., 120 seconds, immersion
  bath composition Zn:    0.8–1.2 g/L
  Ni:    0.5–1.0 g/L
  Mn:   0.8–0.8 g/L
  PO₄:   12–20 g/L
  NO₃:   0.5–8.0 g/L
  The EFC value (points) was measured every 10 treatments, and 0.1 g/L HF was added when the EFC value fell below the lower limit.
(5) Water rinse (tapwater)
  room temperature, 20 seconds, spray
(6) Rinse with de-ionized water (de-ionized water with conductivity = 0.2 micromhos/cm) room temperature, 20 seconds, spray
(7) Drain and Dry
  110° C., 180 seconds This method gave a film weight within the forementioned range over the course of the conversion treatment of 100 sheets at the rate of 1 aluminum sheet per treatment.

As discussed hereinbefore, the conversion treatment method according to the present invention is a superior method for the accurate, highly reproducible measurement of the fluorine concentration that effectively participates in the conversion reactions in acidic conversion treatment baths (effective fluorine concentration).

We claim:

1. A method for controlling the conversion coating activity, for aluminum or aluminum alloy, of a conversion coating solution containing fluoride ions and having a pH below 4, said method comprising steps of:

(I) determining a desired range for effective fluorine concentration (EFC) of the conversion coating solution;

(II) periodically taking a sample from the conversion coating solution during the conversion coating operation;

(III) potentiometrically titrating the sample of the conversion coating solution, without pH adjustment, using a fluoride ion electrode as the indicator electrode, and using as the titrant an aqueous solution containing ions selected from the group consisting of aluminum ions, lanthanum ions, yttrium ions, zirconium ions, gallium ions, cerium ions and beryllium ions, to an inflection point on a potential curve for the fluoride ion electrode;

(IV) determining the EFC of the solution from the quantity of titrant addition up to the inflection point, and, when the EFC of the solution as thus determined is less than the minimum of the desirable range;

(V) adding a source of fluoride ions to the conversion coating solution.

2. A method of claim 1 wherein the EFC is determined according to following equation $$EFC = 400 \times B \times \frac{C}{A}$$

wherein

EFC is the effective fluoride concentration;

A is the quantity of the sample of the conversion coating solution in milliliters;

B Is the concentration of aluminum ions, lanthanum ions, yttrium ions, zirconium ions, gallium ions, cerium ions and beryllium ions in the titrant in mol per liter; and C is the quantity in milliliters of titrant addition to the inflection point: and the EFC of the conversion coating solution is maintained in a range of from about 0.70 to about 7.5 during the conversion coating operation.

3. A method of claim 1 wherein the conversion coating solution is selected from the group consisting of phosphate containing conversion coating solutions and chromate containing conversion coating solutions.

4. A method of claim 3 wherein the conversion coating solution comprises a phosphate containing conversion coating solution.

5. A method of claim 4 wherein the EFC of the conversion coating solution is maintained in the range of about 0.7 to about 7.5 during the conversion coating process.

6. A method of claim 5 wherein the EFC is maintained in the range of from about 0.9 to about 6.5.

7. A method of claim 5 wherein the EFC is maintained in the range of from about 1.1 to about 4.4.

8. A method of claim 2 wherein the EFC is maintained in the range of from about 0.9 to about 6.5.

9. A method of claim 8 wherein the EFC is maintained in the range of from about 1.1 to about 4.4.

* * * * *